US006835736B1

(12) United States Patent
Gunasekera et al.

(10) Patent No.: US 6,835,736 B1
(45) Date of Patent: Dec. 28, 2004

(54) DISCORHABDIN COMPOUNDS AND METHODS OF USE

(75) Inventors: Sarath P. Gunasekera, Vero Beach, FL (US); Ross E. Longley, Tallahassee, FL (US); Shirley A. Pomponi, Fort Pierce, FL (US); Amy E. Wright, Fort Pierce, FL (US)

(73) Assignee: Harbor Branch Oceanographic Institution, Inc., Fort Pierce, FL (US)

( * ) Notice: Subject to any disclaimer, the term of this patent is extended or adjusted under 35 U.S.C. 154(b) by 43 days.

(21) Appl. No.: 10/376,118

(22) Filed: Feb. 28, 2003

(51) Int. Cl.$^7$ ..................... A61K 31/44; C07D 401/14
(52) U.S. Cl. ..................... 514/278; 546/18; 514/278
(58) Field of Search ..................... 546/18; 514/278

(56) References Cited

U.S. PATENT DOCUMENTS

| | | | |
|---|---|---|---|
| 4,206,221 A | 6/1980 | Miller et al. | |
| 4,548,814 A | 10/1985 | Rinehart, Jr. | |
| 4,729,996 A | 3/1988 | Wright et al. | |
| 4,731,366 A | 3/1988 | Munro et al. | |
| 4,737,510 A | 4/1988 | Rinehart, Jr. | |
| 4,808,590 A | 2/1989 | Higa et al. | |
| 4,874,767 A | 10/1989 | Munro et al. | |
| 4,960,790 A | 10/1990 | Stella et al. | |
| 5,157,049 A | 10/1992 | Haugwitz et al. | |
| 5,789,605 A | 8/1998 | Smith et al. | |
| 6,057,333 A | 5/2000 | Gunaskera et al. | |

FOREIGN PATENT DOCUMENTS

WO    WO 9824429    6/1998

OTHER PUBLICATIONS

Balachandran, R. et al., "The potent microtubule–stabilizing agent (+)–discodermolide induces apoptosis in human breast carcinoma cells–preliminary comparisons to paclitaxel" *Anticancer Drugs* 1998, vol. 9, pp. 67–76, abstract.

Kowalski et al., "The microtubule–stabilizing agent discodemolide competitively Inhibits the binding of paclitaxel (Taxol) to tubulin polymers, enhances tubulin nucleation reactions more potently than paclitaxel, and inhibits the growth of paclitaxel–resistant cells" *Mol. Pharmacol.* 1997, vol. 52, pp. 613–622.

Ter Haar et al., "Discodemolide, a cytotoxic marine agent that stabilizes microtubules more potently than taxol" *Biochemistry* 1996, vol. 35, pp. 243–250.

Cheng et al., "Prianosins B, C, and D, Novel Sulfur–Containing Alkaloids with Potent Antineoplastic Activity from the Okinawan Marine Sponge *Prianos melanos*" *J. Org. Chem.* 1988, vol. 53, p. 4621.

Perry et al. "Discorhabdin C, a Highly Cytotoxic Pigment from a Sponge of the Genus *Latrunculia*" *J. Org. Chem.* 1988, vol. 51, p. 5476.

Blunt et al., "Reverse Phase Flash Chromotography: A Method for the Rapid Partitioning of Natural Product Extracts" *J. Nat. Prod.* 1987, vol. 50, p. 290.

Munro et al., *Bioorganic Marine Chemistry*, Scheuer (ed), Verlag Chemie: Heldelberg, vol. 1, Ch. 4.

Kobayashi et al., "Prianosin A, A Novel Antileukemic Akaloid from the Okinawan Marine Sponge *Prianos melanos*" *Tetrahedron Letters* 1987, vol. 28, p. 4939.

Perry et al., "Cytotoxic Pigments from New Zealand Sponges of the Genus *Latrunculia*: Discorhabdins A, B, and C" *Tetrahedron Letters* 1988, vol. 44, p. 1727.

Perry et al., "Discorhabdin D, and Antitumor Alkaloid from the Sponges *Latrunculia brevis* and Prianos sp." *J. Org. Chem.* 1988, vol. 53, p. 4127.

Fuchs, D.A., Johnson, R.K. "Cytologic evidence that taxol, an antineoplastic agent from Taxus brevifolia, acts as amitotic spindle poison" *Cancer Treat. Rep.* 1978, vol. 62, pp. 1219–1222.

Schiff, P.B et al. "Promotion of microtubule assembly in vitro by taxol" *Nature* 1979, vol. 22, pp. 665–667.

Rowinksi, E.K., Donehower, R.C. "Paclitaxel" *N. Engl. J. Med.* 1995, vol. 332, pp. 1004–1014.

Scheuer, P.J. (ed) *Marine Natural Products, Chemical and Biological Perspectives*, Academic Press, New York, 1978–1983, vol. I–V.

Uemura, D. et al. "Norhalichondrin A: An Antitumor Polyether Macrolide from a Marine Sponge" *J. Am. Chem. Soc.* 1985, vol. 107, pp. 4796–4798.

Minale, L. et al. "Natural products from porifera" *Fortscher. Chem. Org. Naturst.* 1976, vol. 33, pp. 1–72.

Faulkner, D. J. "Marine Natural Products" *Natural Products Reports* 2002, vol. 19, pp. 1–48.

Gunasekera, S. P. et al. "Discodermolide: A new bioactive polyhydroxy lactone from the marine sponge *Discodemia dissoluta*" *J. Org. Chem.* 1990, vol. 55, pp. 4912–4915 [correction *J. Org. Chem.* 1991, vol. 56, p. 1346].

Hung et al. "Distinct binding and cellular properties of synthetic (+)– and (–) discodemolides" *Chemistry and Biology* 1994, vol. 1, pp. 67–71.

Hung et al. "(+)–Discodermolide binds to microtubules in stoichiometric ratio to tubulin dimmers, blocks Taxol binding and results in mitotic arrest" *Chemistry and Biology* 1996, vol. 3, pp. 287–293.

Nerenberg, et al., "Total synthesis of immunosuppressive agent (–)–discodermolide" *J. Amer. Chem. Soc.* 1993, vol. 115, pp. 12621–12622.

Smith III et al., "Total synthesis of (–) discodemolide" *J. Amer. Chem. Soc.* 1995, vol. 117, pp. 12011–12012.

Harried et al., "Total synthesis of (–) discodemolide: an application of a chelation–controlled alkylation reaction" *J. Org. Chem.* 1997, vol. 62, pp. 6098–6099.

*Primary Examiner*—Rita Desai
(74) *Attorney, Agent, or Firm*—Saliwanchik, Lloyd & Saliwanchik

(57) ABSTRACT

The subject invention provides novel compositions of biologically active discorhabdin compounds which can advantageously be used for inhibiting pathological cellular proliferation. The compounds of the subject invention have utility for use in the treatment of cancer, including tumors.

62 Claims, 1 Drawing Sheet

DISCORHABDIN COMPOUNDS AND METHODS OF USE

FIELD OF THE INVENTION

This invention relates to discorhabdin compounds and compositions which have useful therapeutic properties. More particularly, the invention provides discorhabdin compounds having antitumor activities, pharmaceutical compositions comprising such compounds, methods for the preparation of the compounds, and compositions and methods of their use.

BACKGROUND OF INVENTION

Various tumor and cancer related diseases afflict animals, including humans. The term "tumor" refers to abnormal masses of new tissue growth which is discordant with the the tissue of origin or of the host's body as a whole. Tumors inflict animals with a variety of disorders and conditions, including various forms of cancer. The seriousness of cancer is well known, e.g. cancer is second only to heart and vascular diseases as a cause of death in man. Cancer is common in a variety of animals, and the prevention and control of the growth of tumors is important to man.

Considerable research and resources have been devoted to oncology and anticancer measures, including chemotherapy. While certain methods and chemical compositions have been developed which aid in inhibiting, remitting, or controlling unwanted cellular proliferation, further anticancer methods and chemical compositions are needed.

It has been found that some natural products and organisms are potential sources for chemical molecules having useful biological activities. For example, the diterpene commonly known as paclitaxel (Taxol®), isolated from several species of yew trees, is a mitotic spindle poison that stabilizes microtubules and inhibits their depolymerization to free tubulin (Fuchs, D. A., R. K. Johnson [1978] *Cancer Treat. Rep.* 62:1219–1222; Schiff, P. B., J. Fant, S. B. Horwitz [19791] *Nature* (London) 22:665–667). Taxol® is also known to have antitumor activity and has undergone a number of clinical trials which have shown it to be effective in the treatment of a wide range of cancers (Rowinski, E. K. R. C. Donehower [1995] *N. Engl. J. Med.* 332:1004–1014). See also, e.g. U.S. Pat. Nos. 5,157,049; 4,960,790; and 4,206,221.

Marine life has been the source for the discovery of compounds having varied biological activities. Some of the United States patents which have issued for such inventions are as follows: U.S. Pat. No. 4,548,814 for didemnins, having antiviral activity, were isolated from a marine tunicate; U.S. Pat. No. 4,729,996 discloses compounds, having antitumor properties, that were isolated from marine sponges *Teichaxinella morchella* and *Ptilocaulis walpersi*; U.S. Pat. No. 4,808,590 discloses compounds, having antiviral, antitumor, and antifungal properties, isolated from the marine sponge Theonella sp.; and U.S. Pat. No. 4,737,510 discloses compounds, having antiviral and antibacterial properties, isolated from the Caribbean sponge *Agelas coniferin*.

A number of publications disclose organic compounds derived from marine sponges including Scheuer, P. J. (ed.) *Marine Natural Products, Chemical and Biological Perspectives*, Academic Press, New York, 1978–1983, Vol. I–V; Uemura, D., K. Takahashi, T. Yamamoto, C. Katayama, J. Tanaka, Y. Okumura, Y. Hirata (1985) *J. Am. Chem. Soc.* 107:4796–4798; Minale, L. et al. (1976) *Fortschr. Chem. org. Naturst.* 33:1–72; Faulkner, D. J. (2002) *Natural Products Reports* 19:1–48; Gunasekera, S. P., M. Gunasekera, R. E. Longley and G. K. Schulte (1990) "Discodernolide: A new bioactive polyhydroxy lactone from the marine sponge *Discodermia dissoluta*" *J. Org. Chem.*, 55:4912–4915 [correction (1991) *J. Org. Chem.* 56:1346]; Hung, Deborah T., Jenne B. Nerenberg, Stuart Schreiber (1994) "Distinct binding and cellular properties of synthetic (+)- and (−) discodermolides" *Chemistry and Biology* 1:67–71; Hung, Deborah T., Jie Cheng, Stuart Schreiber (1996) (+)-Discodermolide binds to microtubules in stoichiometric ratio to tubulin dimers, blocks Taxol binding and results in mitotic arrest" *Chemistry and Biology* 3:287–293; Nerenberg, Jennie B., Deborah T. Hung, Patricia K. Somers, Stuart L. Schreiber (1993) "Total synthesis of immunosuppressive agent (−)-discodemolide" *J. Amer. Chem. Soc.* 115:12621–12622; Smith III, Amos B., Yuping Qiu, David R. Jones, Karoru Kobayashi (1995) "Total synthesis of (−) discodernolide" *J. Amer. Chem. Soc.* 117:12011–12012; Harried, Scott H., Ge Yang, Marcus A. Strawn, David C. Myles (1997) "Total synthesis of (−)-discodermolide: an application of a chelation-controlled alkylation reaction" *J. Org. Chem.* 62:6098–6099; Balachandran, R., ter Haar, E., Welsh, M. J., Grant, S. G., and Day, B. W. (1998) "The potent microtubule-stabilizing agent (+)-discodermolide induces apoptosis in human breast carcinoma cells-preliminary comparisons to paclitaxel." *Anticancer Drugs* 9: 67–76 and references cited therein. U.S. Pat. No. 4,808,590 discloses compounds, having antiviral, antitumor, and antifungal properties, isolated from the marine sponge Theonella sp. (International Patent Application No. WO 9824429; Kowalski, R. J., P. Giannakakou, S. P. Gunasekera et al. (1997) *Mol. Pharmacol* 52:613–622; ter Haar, E., R. J. Kowalski, E. Hamel et al. (1996) *Biochemistry* 35:243–250; Stafford, J. A. and M. M. Mehrotra (1995) *Chemtract: Org. Chem.* 8:41–47; and U.S. Pat. No. 5,789,605.

Discorhabdin compounds have been produced from marine sponges as disclosed in U.S. Pat. Nos. 4,731,366; 4,874,767; and 6,057,333 and have been discussed in various publications including: Perry, N. B. et al. (1986) *J. Org. Chem.* 51:5476; Blunt, J. W. et al. (1987) *J. Nat. Prod.* 50:290; Munro, M. H. G. et al. (1987) *Bioorganic Marine Chemistry*, Scheuer, P. J., Ed., Verlag Chemie: Heidelberg, Vol. 1, Chapter 4; Kobayashi, J. et al. (1987) *Tetrahedron Letters* 28:4939; Perry, N. B. et al. (1988) *Tetrahedron Letters* 44:1727; Perry, N. B. et al. (1988) *J. Org. Chem.* 53:4127; and Cheng et al. (1988) *J. Org. Chem.* 53:4610.

The previously known discorhabdins (A→R), have an iminoquinone and a spiro-enone or spiro-dienone system, and are believed to be formed by the combination of a molecule of substituted tyrosine and a molecule of tryptamine.

The present invention, utilizing sponges as a source material, provides the art with new biologically active compounds and new pharmaceutical compositions useful for the control of unwanted cellular proliferation as antitumor agents. The present invention has added to the arsenal of phrmaceutical compounds by the discovery of novel compounds isolatable from extracts of marine sponges of the family Desmacididae.

BRIEF SUMMARY

The subject invention provides discorhabdin compounds having advantageous biological activities. Specifically, in one embodiment, the discorhabdin compounds and compositions of the subject invention can be used in the treatment of an animal (including humans) hosting cancer cells, including, for example, inhibiting the growth of tumor cells in a mammalian host. More particularly, the subject compounds can be used for inhibiting in a human the growth of tumor cells, including cancer cells of the pancreas, breast, colon, CNS, ovarian, renal, prostrate, lung, leukemia and melanoma cells.

Also provided according to the subject invention are compositions containing the biologically active discorhabdin compounds, as well as methods for the preparation and use of the compounds and compositions.

Other advantages and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

DETAILED DISCLOSURE

Figure 1:
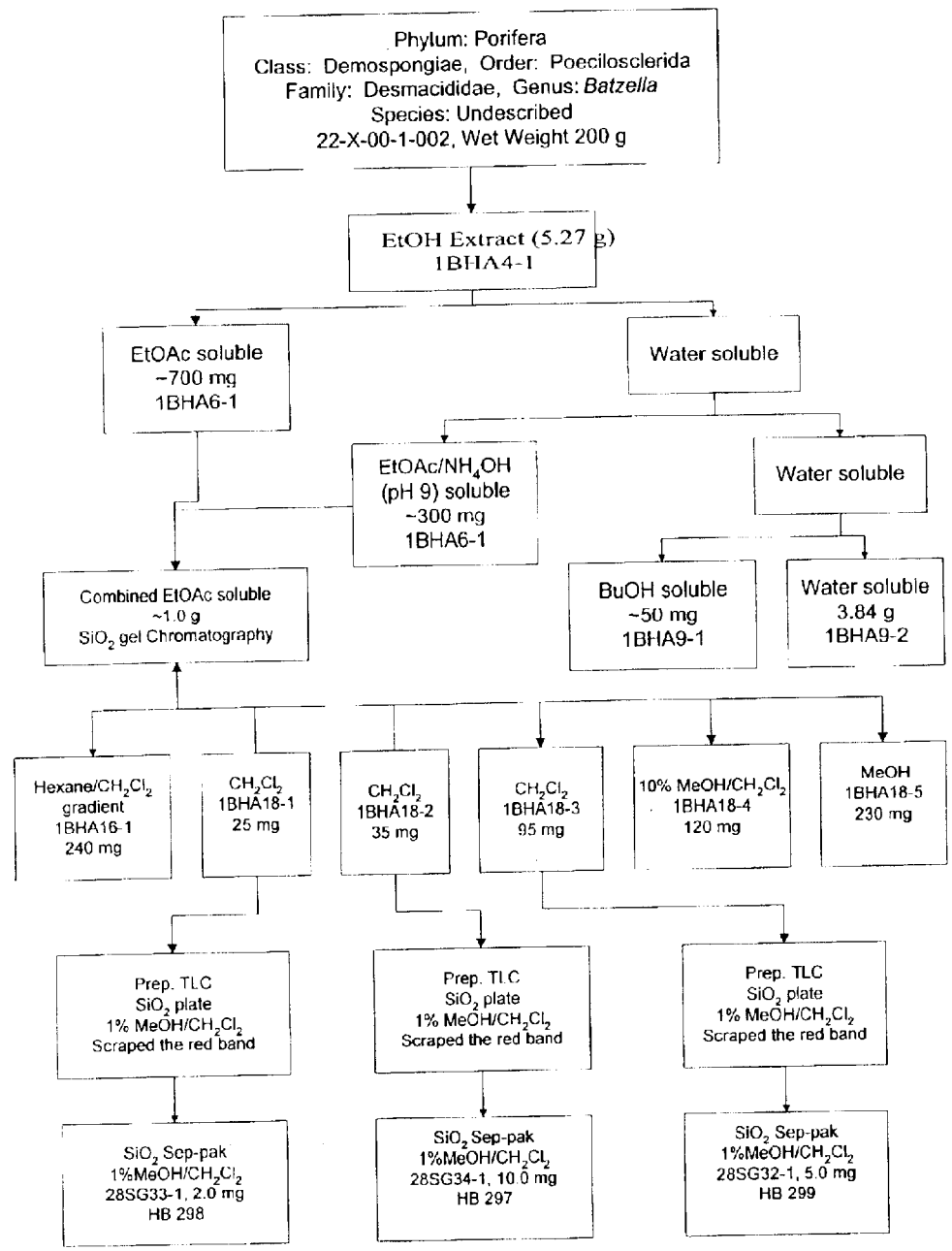
FIG. 1 shows an isolation scheme for the compounds of the subject invention.

The subject invention pertains, in part, to novel discorhabdin compounds and the use of these compounds to prevent pathological cellular proliferation. In a specific embodiment, the subject invention pertains to novel compounds known as discorhabdins S, T, and U, as well as their analogs. The compounds of the subject invention can be formulated into pharmaceutical compositions and can be used to treat tumors and others forms of pathological cellular proliferation.

The present invention, utilizing sponges as a source material, provides the art with new biologically active compounds and new pharmaceutical compositions useful as inhibitors of unwanted cellular proliferation, including as antitumor agents. The present invention has added to the arsenal of phrmaceutical compounds by the discovery of novel compounds isolatable from extracts of marine sponges of the family Desmacididae.

The specifics of the sponge which serves as a source for compounds of the subject invention are as follows:

| Phylum | Porifera |
| --- | --- |
| Class | Demospongiae |
| Order | Poecilosclerida |
| Family | Phoriospongiidae |
| Genus | Batzella |
| Species | undescribed |

The sponge has been assigned to the genus Batzella, as described and discussed by van Soest et al. (1996, pp. 95–97, Bulletin de I'Institut Royal des Sciences Naturelles de Belgique, Biologie, 66 suppl:89–101). The sponge has a detachable ectosome and a spicule skeleton of strongyles of one size category. Some of the strongyles have malformed tips. The sponge incorporates sediment into its skeleton. There are numerous papillae scattered over the surface of the sponge. The sponge is dark brown to black when alive, brown when preserved in ethanol.

A taxonomic reference sample has been deposited in the Harbor Branch Oceanographic Museum, catalog number 003:00983 (22-X-00-1-002).

Compounds useful according to the subject invention can be isolated by various fractionation and chromatographic techniques from the extracts obtained as disclosed herein. Preferred isolation procedures include various chromatography techniques, such as countercurrent chromatography, with suitable columns including multi-layer planetary coil columns. A variety of solvents are available for use as single or mixed eluents, such as tetrahydrofuran, methanol, ethyl acetate, acetonitrile, n-propanol, n-butmnol, water, and equivalent solvents. Further purifications using such procedures may also be carried out on the recovered extractions. Preferred isolation techniques for further purifications include chromatographic operations such as high-pressure liquid chromatography (HPLC) with suitable columns and suitable solvents. FIG. 1 shows an isolation scheme for the compounds of the subject invention.

Discorhabdins S, T, and U are novel compounds which are quite different from other known discorhabdins. The molecular structures of discorhabdins S, T, U are closely related. Each differs only in their state of saturation of the isolated double bonds in the heteroaromatic rings. Although the compounds of the subject invention have some structural similarities to the previously known discorhabdins (A→R), discorhabdins S, T, and U contain an unusual vinylic thiomethyl ether functionality in the molecular structure. This functionality is absent in all other known discorhabdins. The N-methyl functionality present in discorhabdins S, T, and U is present in discorhabdin P; however, the combination of N-methyl and S-methyl functional groups are present only in discorhabdins S, T, and U.

Thus, the subject invention pertains, in part, to compounds having the following structural formulas:

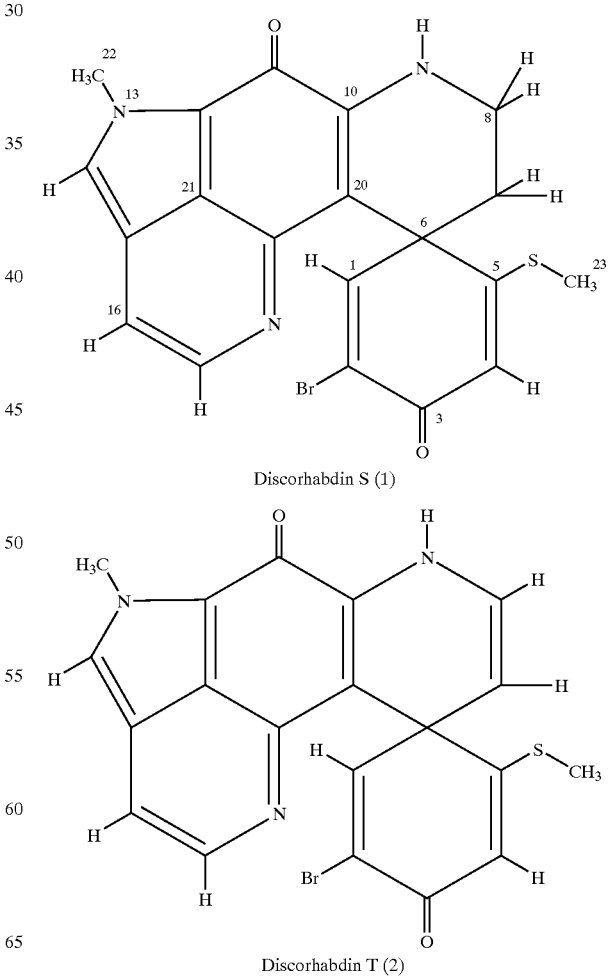

Discorhabdin S (1)

Discorhabdin T (2)

Discorhabdin U (3)

These compounds have been found to have the following characteristics:

Discorhabdin S (1)
Red powder
HRLSIMS (M$^+$+H) appeared at 442.0261 ($C_{20}H_{17}{}^{79}BrN_3O_2S$, Δ 3.6 mmu) and 444.0470 ($C_{20}H_{17}{}^{81}BrN_3O_2S$)
UV(MeOH) λ max 422 (log ε 4.14), 400 (3.94), 305 (4.04), 260 (4.27), 225 (4.54) nm
IR (NaCl, Neat) ν max 3385, 3043, 2924, 1858, 1637,1602, 1543, 1498, 1348, 1318, 1240, 1017 and 735 cm$^{-1}$
$^1$H NMR (500 MHz, CDCl$_3$/10% CD$_3$OD) δ 8.08 (1H, d, J=5.8 Hz, H-17), 7.54 (1H, s, H-14), 7.50 (H, s, H-1)), 7.15 (1H, d, J=5.8Hz, H-16),6.14 (1H, s, H-4),4.19 (3H, s, H-22), 3.73, 3.46 (2H, m, H-8), 2.23, 2.02 (2H, m, H-7), 2.15 (3H, s, H-23).
$^{13}$C NMR (125.7 MHz, CDCl$_3$/10% CD$_3$OD) δ 176.6 (s, C-5), 175.0 (s, C-3), 165.9 (s, C-11), 155.5 (d, C-1), 146.1 (s, C-19), 145.9 (s, C-10), 142.3 (d, C-17), 130.6 (d, C-14), 123.5 (s, C-15), 122.4 (s, C-2), 119.1 (s, C-12), 118.6 (s, C-21), 117.7 (d, C-4), 111.0 (d, C-16), 104.7 (s, C-20), 47.5 (s, C-6), 37.9 (t, C-7), 37.2 (q, C-22), 36.9 (t, C-8), 14.7 (q, C-23).

Discorhabdin T (2)
Red powder
HREIMS (M$^+$) appeared at 438.9996 ($C_{20}H_{14}{}^{79}BrN_3O_2S$, Δ 1 mmu) and 440.9869 ($C_2OH_{14}{}^{18}BrN_3O_2S$)
UV (MeOH) λ max 432 (log ε 3.65), 412 (3.55), 305 (3.65), 245 (3.97), 225 (4.11nm
IR (NaCl, Neat) ν max 3375, 2874, 1637, 1609, 1554, 1476, 1315, 1265, 093 and 805 cm$^{-1}$
$^1$H NMR (500 MHz, CDCl$_3$/10% CD$_3$OD) δ 8.17 (1H, d, J=5.8 Hz, H-17), 7.64 (1H, s, H-14), 7.62 (H, s, H-1), 7.30 (1H, d, J=5.8 Hz, H-16), 6.43 (1H, d, J=7.5 Hz, H-8), 5.91 (1H, s, H-4), 4.25 (3H, s, H-22), 4.10 (1H, d, J=7.5 Hz, H-7), 2.18 (3H, s H-23).
$^{13}$C NMR (125.7 MHz, CDCl$_3$/10% CD$_3$OD) δ 177.0 (s, C-5), 176.5 (s, C-3), 165.1 (s, C-11), 154.1 (d, C-1), 146.1 (s, C-19), 143.1 (d, C-17), 139.0 (s, C-10) 130.7 (d, C-14), 125.8 (d, C-8), 123.9 (s, C-15), 119.7 (s, C-12), 119.1 (s, C-21), 119.0 (s, C-2), 114.5 (d, C-4), 113.1 (d, C-16), 109.3 (s, C-20), 103.5 (d, C-7), 50.2 (s, C-6), 37.4 (q, C-22), 14.8 (q, C-23).

Discorhabdin U (3)
Red powder
HRLSLMS (M$^+$ +H) appeared at 442.0275 ($C_{20}H_{17}{}^{79}BrN_3O_2S$, Δ 5 mmu) and 444.0052 ($C_{20}H_{17}{}^{81}BrN_3O_2S$)
UV (MeOH) λ max 425 (log ε 3.12), 340 (3.95), 287 (4.01), 242 (4.22), 205 (4.42nm
IR (NaCl, Neat) ν max 3328, 2924, 1637, 1602, 1558, 1479, 1435, 1280, 1010 and 668 cm$^{-1}$
$^1$H NMR (500 MHz, CDCl$_3$) δ 7.57 (1H, s, H-1), 6.99 (1H, br s, H-9), 6.63 (1H, s, H-14), 6.38 (1H, d, J=7.5 Hz, H-8), 5.88 (1H, s, H-4), 4.09 (1H, d, J=7.5 Hz, H-7), 3.93 (2H, t, J=8.0 Hz, H-17), 3.90 (3H, s, H-22), 2.58 (2H, t, J=8.0 Hz, H-16), 2.29 (3H, s, H-23).
$^{13}$C NMR (125.7 MHz, CDCl$_3$) δ 176.6 (s, C-5), 175.2 (s, C-3), 169.4 (s, C-I1), 154 (d, C-1), 154.0 (s, C-19), 137.1 (s, C-10), 128.4 (d, C-14), 125.6 (d, C-8), 122.3 (s, C-21), 122.0 (s, C-12), 119.0 (s, C-2), 117.2 (s, C-15), 114.6 (d, C-4), 109.0 (s, C-20), 104.6 (d, C-7), 50.3 (t, C-17), 49.7 (s, C-6), 35.4 (q, C-22), 17.9 (t, C-16), 15.1 (q, C-23).

Included within the scope of the subject invention are salts and analogs of Compounds 1, 2, and 3. The salts of the subject invention may be, for example, Cl$^{31}$, Br$^-$, CH$_3$COO$^-$, HSO$_3$O$^-$, citrate or tartarate.

As used in this application, the term "analogs" refers to equivalent compounds which are substantially the same as another compound but which may have been modified by, for example, adding side groups. Salts are also within the scope of the present invention. Analogs of the exemplified compounds can be readily prepared using commonly known, standard reactions. These standard reactions include, but are not limited to, hydrogenation, methylation, acetylation, and acidification reactions.

Preferred embodiments of the subject invention include discorhabdin S (1), discorhabdin T (2) and discorhabdin U (3). Additional preferred embodiments include 16,17-dihydrodiscorhabdin (4) and salts (Cl$^-$, Br$^-$, CH$_3$COO$^-$, HSO$_3$O$^-$, oxalate, tartarate, etc.) of the protonated compounds 1, 2, 3, and 4.

16,17-Dihydrodiscorhabdin S (4)

Further preferred embodiments include:
a) 13-NR analogues of compounds 1→4 (R=H, C$_{2-5}$ alkyl)
b) 13-NR analogues of compounds 1→4 (R=COR$_1$, where R$_1$ lower alkyl or phenyl)
c) 2-debromoanalogues of compounds 1→4
d) 5-thiols of compounds 1→4
e) 5-SR analogues of compounds 1→4 (R=C$_{2-5}$ alkyl; COR$_1$ where R$_1$=lower alkyl or phenyl)
f) 5-OR analogues of compounds 1→4 (R=H, or lower alkyl, or phenyl)
g) 1,2-dihydroanalogues of compounds 1→4
h) 4,5-dihydroanalogues of compounds 1→4 i) 1,2,4,5-tetrahydroanalogues of compounds 1→4 j) 3-H,OR analogues of compounds 1→4 (where R=H, or lower alkyls; $COR_1$ where $R_1$=lower alkyls or phenyl)

Accordingly, in preferred embodiments the subject invention provides antiproliferative methods and compositions utilizing compounds, and/or salts or analogs thereof, wherein the compounds have the following structure:

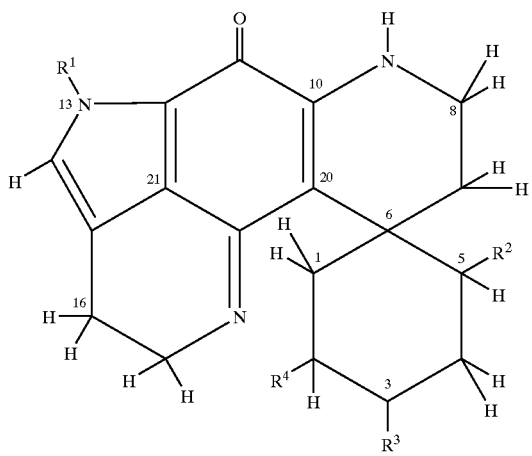

wherein $R_1$ is selected from the group consisting of hydrogen, $C_1$–$C_5$ alkyl, and $COR^5$; wherein $R^5$ is selected from the group consisting of $C_1$–$C_5$ alkyl and phenyl; $R^2$ is selected from the group consisting of $SR^6$, $SCOR^7$, and $OR^8$; wherein $R^6$ is selected from the group consisting of $C_1$–$C_5$ alkyl and phenyl; $R^7$ is selected from the group consisting of $C_1$–$C_5$ alkyl and phenyl; and $R^8$ is selected from the group consisting of hydrogen, $C_1$–$C_5$ alkyl, $COR^5$ and phenyl;

$R^3$ is selected from the group consisting of hydrogen, $OR^9$, and $OCOR^{10}$; wherein $R^9$ is selected from the group consisting of hydrogen and $C_1$–$C_5$ alkyl; and $R^{10}$ is selected from the group consisting of $C_1$–$C_5$ alkyl and phenyl; or $R^3$ is connected to C3 with a double bond in which case $R^3$ is oxygen;

$R^4$ is selected from the group consisting of hydrogen and halides; and wherein each of the bonds between C1–C2, C4–C5, C7–C8, and C16–C17 may, independently, be either single or double bonds.

As described herein, the invention comprises the use of the new compounds of the subject invention for inhibiting unwanted cellular proliferation and, in a preferred embodiment, for the inhibition of tumor growth. Thus, one aspect of the subject invention is a method for the antitumor treatment of a human in need of such treatment, i.e., a human hosting cancer cells, including breast, colon, or lung tumor cells, leukemia cells, CNS cancer cell lines, melanoma cell lines, ovarian cancer cell lines, renal cancer cell lines, and prostate cancer cell lines.

In accordance with the invention, methods for inhibiting tumors in a host comprise contacting tumor cells with an effective amount of the new pharmaceutical compositions of the invention. The tumor cells inhibited by the invention are those which are susceptible to the subject compounds described herein or compositions comprising those compounds.

A more complete understanding of the invention can be obtained by reference to preferred embodiments of the invention which are illustrated by the following specific examples of compounds, compositions, and methods of the invention. It will be apparent to those skilled in the art that the examples involve use of materials and reagents that are commercially available from known sources, e.g., chemical supply houses, so no details are given respecting them.

Following are examples which illustrate procedures for practicing the invention. These examples should not be construed as limiting. All percentages are by weight and all solvent mixture proportions are by volume unless otherwise noted.

EXAMPLE 1

Antitumor Activity

Extracts and compounds were analyzed as to their effects on proliferation of A549 human adenocarcinoma, PANC-1 human pancreatic and P388 murine leukemia cell lines. P388 and NCI/ADR cells were obtained from Dr. R. Camalier, National Cancer Institute, Bethesda, Md., and A549 and PANC-1 cells were obtained from American Type Culture Collection, Rockville, Md. All cell lines were maintained in Roswell Park Memorial Institute (RPMI) medium 1640 supplemented with 10% fetal bovine sernm. All cell lines were cultured in plastic tissue culture flasks and kept in an incubator at 37° C. in humidified air containing 5% $CO_2$. Prior to testing, antibiotic-free stock cultures of each of the cell lines were subcultured to 106 cells/ml by dilution in fresh growth medium at 2 to 3 day intervals.

To assess the antiproliferative effects of extracts and compounds against the P388 cell line, 200 µl cultures (96-well tissue culture plates, Nunc, Denmark) are established at 1×10⁵ cells/ml in drug-free medium or medium containing the test agent at 10.0, 1.0, 0.10 and 0.010 µg/ml. Solvent for all dilutions ethanol. All experimental cultures are initiated in medium containing gentamycin su fate (50 µg/ml; Schering Corporation, Kenilworth, N.J.). After 48-h exposures, P388 cells are enumerated using 3-[4,5-dimethylthiazol-2-yl]-2,5-diphenyltetrazolium bromide (MTT) as described below (M. C. Alley et al., 1988, Cancer Res. 48:589.

Similar procedures are utilized for A549 and PANC-1 cells which require an additional 48 hour exposure prior to MTT addition. Results are expressed as percent inhibition compared to the negative (no drug) control. Positive drug controls are included to monitor drug sensitivity of each of the cell lines. These include varying dilutions of 5-fluorouracil and adriamycin.

To quantitate the effects of pure compounds on cell proliferation and resulting $IC_{50}$ values, 75 µl of warm growth media containing 5 mg/ml MTT is added to each well, cultures returned to the incubator, and left undisturbed for 90 minutes. To spectrophotometrically quantitate formation of reduced formazan, plates are centrifuged (900×g, 5 minutes), culture fluids removed by aspiration, and 200 µl of acidified isopropanol (2 ml concentrated HCl/liter isopropanol) added per well. The absorbance of the resulting solutions is measured at 570 nm with a plate reader (TECAN Spectra II Plate Reader, TECAN U.S., Research Triangle Park, NC). The absorbance of test wells is divided by the absorbance of drug-free wells, and the concentration of agent that results in 50% of the absorbance of untreated cultures ($IC_{50}$is determined by linear regression of logit-transformed data (D. J. Finney, Statistical Method in Biological Assay, third ed., pp.316–348, Charles Griffin Co., London, 1978. A linear relationship between tumor cell number and formazan production has been routinely observed over the range of cell densities observed in these experiments. The two standard drug controls (indicated above) are included in each assay as a check to monitor the drug sensitivity of each of the cell lines and $IC_{50}$ values are determined for each drug-cell combination. The activities of the compounds as shown in Table 1.

TABLE 1

| Discorhabdin | Activity ($IC_{50}$) µg/ml | | | |
| --- | --- | --- | --- | --- |
| | PANC-1 | P-388 | A549 | NCI/ADR |
| S | 2.6 | 3.08 | >5 | >5 |
| T | 0.7 | >5 | >5 | >5 |
| U | 0.069 | 0.17 | 0.34 | 0.22 |

EXAMPLE 2

Uses, Formulations, and Administrations

Therapeutic and prophylactic application of the discorhabdin compounds, and compositions comprising them, can be accomplished by any suitable method and technique presently or prospectively known to those skilled in the art. Further, the compounds of the invention have use as starting materials or intermediates for the preparation of other useful compounds and compositions. The compounds of the invention are useful for various non-therapeutic and therapeutic purposes.

In one embodiment, the compounds of the subject invention are effective for inhibiting cell growth. Because of the antiproliferative properties of the compounds, they are useful to prevent unwanted cell growth in a wide variety of settings including in vitro uses. They are also useful as standards and for teaching demonstrations. They can also be used as ultraviolet screeners in the plastics industry since they effectively absorb UV rays. As disclosed herein, they are also useful prophylactically and therapeutically for treating cancer cells in animals and humans.

The dosage administration to a host in the above indications will be dependent upon the identity of the cancer cells, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The compositions of the invention are advantageously used in a variety of forms, e.g., tablets, ointments, capsules, pills, powders, aerosols, granules, and oral solutions or suspensions and the like containing the indicated suitable quantities of the active ingredient. Such compositions are referred to herein and in the accompanying claims generically as "pharmaceutical compositions." Typically, they can be in unit dosage form, namely, in physically discrete units suitable as unitary dosages for human or animal subjects, each unit containing a predetermined quantity of active ingredient calculated to produce the desired therapeutic or prophylactic effect in association with one or more pharmaceutically acceptable other ingredients, e.g. diluent or carrier.

Where the pharmaceutical compositions are aerosols, the active ingredients can be packaged in pressurized aerosol containers with a propellant, e.g. carbon dioxide, nitrogen, propane, etc. with the usual adjuvants such as cosolvents, wetting agents, etc.

Where the pharmaceutical compositions are ointments, the active ingredient can be mixed with a diluent vehicle such as cocoa butter, viscous polyethylene glycols, hydrogenated oils, and such mixtures can be emulsified if desired.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for inhibiting the growth of cancer cells, said method comprising administering to said cells an effective amount of a compound, or a salt thereof, wherein said compound has the following structure:

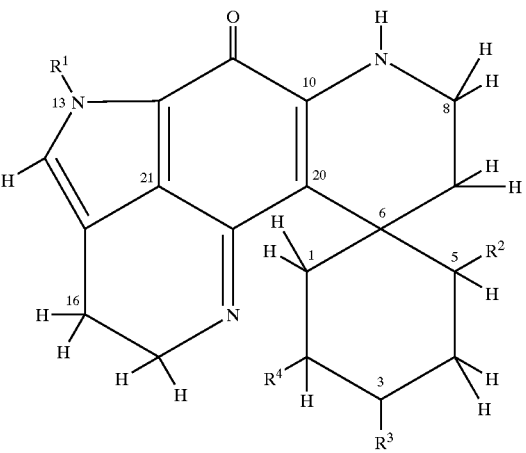

wherein $R^1$ is selected from the group consisting of hydrogen, $C_1$–$C_5$ alkyl, and $COR^5$; wherein $R^5$ is selected from the group consisting of $C_1$–$C_5$ alkyl and phenyl; $R^2$ is selected from the group consisting of SR[6], SCOR[7], and OR[8]; wherein R[6] is selected from the group consisting of $C_1$–$C_5$ alkyl and phenyl; R[7] is selected from the group consisting of $C_1$–$C_5$ alkyl and phenyl; and R[8] is selected from the group consisting of hydrogen, $C_1$–$C_5$ alkyl, COR[5] and phenyl;

R[3] is selected from the group consisting of hydrogen, OR[9], and OCOR[10]; wherein R[9] is selected from the group consisting of hydrogen and $C_1$–$C_5$ alkyl; and R[10] is selected from the group consisting of $C_1$–$C_5$ alkyl and phenyl; or R[3] is connected to C3 with a double bond in which case R[3] is oxygen;

R[4] is selected from the group consisting of hydrogen and halides; and wherein each of the bonds between C1–C2, C4–C5, C7–C8, and C16–C17 may, independently, be either single or double bonds.

2. The method, according to claim 1, wherein R[1] is $CH_3$.

3. The method, according to claim 1, wherein R[2] is $SCH_3$.

4. The method, according to claim 1, wherein has R[3] as oxygen connected to C3 with a double bond forming a ketone.

5. The method, according to claim 1, wherein R[4] is Br.

6. The method, according to claim 1, wherein R[1] is $CH_3$, R[2] is $SCH_3$, R[3] is oxygen connected to C3 with a double bond and R[4] is Br.

7. The method, according to claim 1, wherein C1–C2, C4–C5 and C16–C17 are all connected with double bonds.

8. The method, according to claim 1, wherein C1–C2, C4–C5, C7–C8 and C16–C17 are all connected with double bonds.

9. The method, according to claim 1, wherein C1–C2, C4–C5 and C7–C8 are all connected with double bonds.

10. The method, according to claim 1, wherein C1–C2 and C4–C5 are connected with double bonds.

11. The method, according to claim 1, wherein said compound has the following structure:

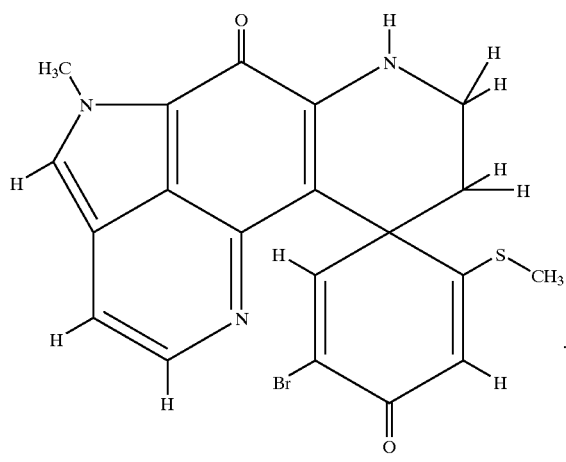

Discorhabdin S

12. The method, according to claim 1, wherein said compound has the following structure:

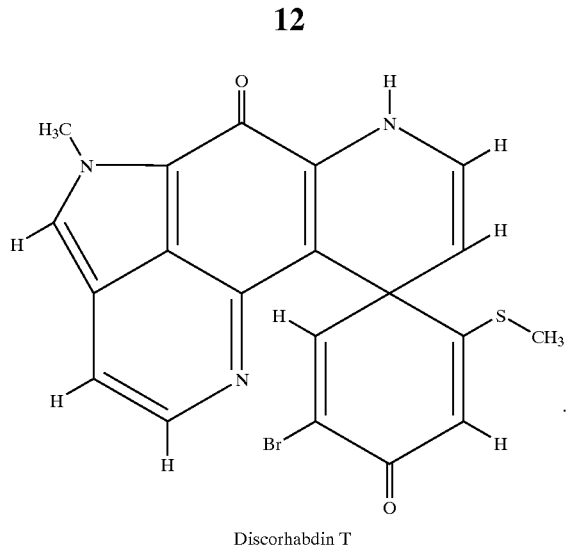

Discorhabdin T

13. The method, according to claim 1, wherein said compound has the following structure:

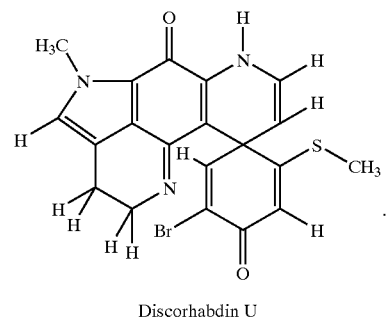

Discorhabdin U

14. The method, according to claim 1, wherein said compound has the following structure:

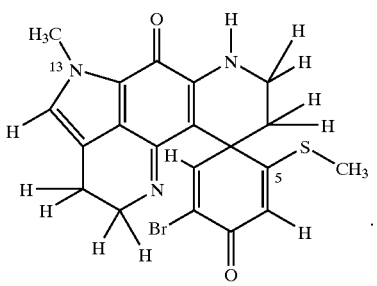

16, 17-Dihydrodiscorhabdin S

15. The method, according to claim 1, wherein said compound contains an N-methyl group at N13 and an S-methyl group at C5.

16. The method, according to claim 1, wherein said compound contains a vinylic thiomethyl ether at the C5 position.

17. The method, according to claim 1, wherein said salt is a $Cl^-$, $Br^-$, $CH_3COO^-$, $HSO_3O^-$, oxalate, citrate, or tartarate salt.

18. The method, according to claim 1, wherein said cancer cells are selected from the group consisting of leukemia, lung cancer, colon cancer, CNS cancer, melanoma, ovarian cancer, renal cancer, prostate cancer, breast cancer and pancreatic cancer.

19. The method, according to claim 1, wherein said compound is administered as a pharmaceutical composition, said pharmaceutical composition comprising an effective amount of one or more compounds of claim 1 and an acceptable carrier.

20. The method, according to claim 1, wherein said compound has the following spectroscopic data:

HRLSIMS (M$^+$ +H) appeared at 442.0261 (C$_{20}$H$_{17}$$^{79}$BrN$_3$O$_2$S, Δ3.6 mmu) and 444.0470 (C$_{20}$H$_{17}$$^{81}$BrN$_3$O$_2$S)

UV (MeOH) λ max 422 (log ε 4.14), 400 (3.94), 305 (4.04), 260 (4.27), 225 (4.54) nm IR (NaCl, Neat) ν max 3385, 3043, 2924, 1858, 1637, 1602, 1543, 1498, 1348, 1318, 1240, 1017 and 735 cm$^{-1}$ $^1$H NMR (500 MHz, CDCl$_3$/10% CD$_3$OD) δ 8.08 (1H, d, J=5.8 Hz, H-17), 7.54 (1H, s, H-14), 7.50 (H, s, H-1), 7.15 (1H, d, J=5.8 Hz, H-16), 6.14 (1H, s, H-4), 4.19 (3H, s, H-22), 3.73, 3.46 (2H, m, H-8), 2.23, 2.02 (2H, m, H-7), 2.15 (3H, s, H-23)

$^{13}$C NMR (125.7 MHz, CDCl$_3$/10% CD$_3$OD) δ 176.6 (s, C-5), 175.0 (s, C-3), 165.9 (s, C-11), 155.5 (d, C-1), 146.1 (s, C-19), 145.9 (s, C-$^{10}$), 142.3 (d, C-17), 130.6 (d, C-14), 123.5 (s, C-15), 122.4 (s, C-2), 119.1 (s, C-12), 118.6 (s, C-21), 117.7 (d, C-4), 111.0 (d, C-16), 104.7 (s, C-20), 47.5 (s, C-6), 37.9 (t, C-7), 37.2 (q, C-22), 36.9 (t, C-8), 14.7 (q, C-23).

21. The method, according to claim 1, wherein said compound has the following spectroscopic data:

HREIMS (M$^+$) appeared at 438.9996 (C$_{20}$H$_{14}$$^{79}$BrN$_3$O$_2$S, Δ 1 mmu) and 440.9869 (C$_{20}$H$_{14}$$^{81}$BrN$_3$O$_2$S)

UV (MeOH) λ max 432 (log ε 3.65), 412 (3.55), 305 (3.65), 245 (3.97), 225 (4.11) nm IR (NaCl, Neat) ν max 3375, 2874, 1637, 1609, 1554, 1476, 1315, 1265, 093 and 805 cm$^{-1}$ $^1$H NMR (500 MHz, CDCl$_3$/10% CD$_3$OD) δ 8.17 (1H, d, J=5.8 Hz, H-17), 7.64 (1H, s, H-14), 7.62 (H, s, H-1), 7.30 (1H, d, J=5.8 Hz, H-16), 6.43 (1H, d, J=7.5 Hz, H-8), 5.91 (1H, s, H-4), 4.25 (3H, s, H-22), 4.10 (1H, d, J=7.5 Hz, H-7), 2.18 (3H, s, H-23)

$^{13}$C NMR (125.7 MHz, CDCl$_3$/10% CD$_3$OD) δ 177.0 (s, C-5), 176.5 (s, C-3), 165.1 (s, C-11), 154.1 (d, C-1), 146.1 (s, C-19), 143.1 (d, C-17), 139.0 (s, C-10), 130.7 (d, C-14), 125.8 (d, C-8), 123.9 (s, C-15), 119.7 (s, C-12), 119.1 (s, C-21), 119.0 (s, C-2), 114.5 (d, C-4), 113.1 (d, C-16), 109.3 (s, C-20), 103.5 (d, C-7), 50.2 (s, C-6), 37.4 (q, C-22), 14.8 (q, C-23).

22. The method, according to claim 1, wherein said compound has the following spectroscopic data:

HRLSIMS (M$^+$ +H) appeared at 442.0275 (C$_{20}$H$_{17}$$^{79}$BrN$_3$O$_2$S, Δ 5 mmu) and 444.0052 (C$_{20}$H$_{17}$$^{81}$BrN$_3$O$_2$S)

UV (MeOH) λ max 425 (log ε 3.12), 340 (3.95), 287 (4.01), 242 (4.22), 205 (4.42) nm IR (NaCl, Neat) ν max 3328, 2924, 1637, 1602, 1558, 1479, 1435, 1280, 1010 and 668 cm$^{-1}$ $^1$H NMR (500 MHz, CDCl$_3$) δ 7.57 (1H, s, H-1), 6.99 (1H, br s, H-9), 6.63 (1H, s, H-14), 6.38 (1H, d, J=7.5 Hz, H-8), 5.88 (1H, s, H-4), 4.09 (1H, d, J=7.5 Hz, H-7), 3.93 (2H, t, J=8.0 Hz, H-17), 3.90 (3H, s, H-22), 2.58 (2H, t, J=8.0 Hz, H-16), 2.29 (3H, s, H-23)

$^{13}$C NMR (125.7 MHz, CDCl$_3$) δ 176.6 (s, C-5), 175.2 (s, C-3), 169.4 (s, C-11), 154.2 (s, C-1), 154.0 (s, C-19), 137.1 (s, C-10), 128.4 (d, C-14), 125.6 (d, C-8), 122.3 (s, C-21), 122.0 (s, C-12), 119.0 (s, C-2), 117.2 (s, C-15), 114.6 (d, C-4), 109.0 (s, C-20), 104.6 (d, C-7), 50.3 (t, C-17), 49.7 (s, C-6), 35.4 (q, C-22), 17.9 (t, C-16), 15.1 (q, C-23).

23. A compound, or a salt thereof, wherein said compound has the following structure:

[Chemical structure diagram showing a polycyclic compound with labeled positions 1-23, substituents R$^1$, R$^2$, R$^3$, R$^4$, and various H atoms]

wherein R$^1$ is selected from the group consisting of hydrogen, C$_1$–C$_5$ alkyl, and COR$^5$; wherein R$^5$ is selected from the group consisting of C$_1$–C$_5$ alkyl and phenyl;

wherein R$^2$ is selected from the group consisting of SR$^6$, SCOR$^7$, and OR$^8$;

wherein R$^6$ is selected from the group consisting of C$_1$–C$_5$ alkyl and phenyl;

R$^7$ is selected from the group consisting of C$_1$–C$_5$ alkyl and phenyl; and R$^8$ is selected from the group consisting of hydrogen, C$_1$–C$_5$ alkyl, COR$^5$ and phenyl;

wherein R$^3$ is selected from the group consisting of hydrogen, OR$^9$, and OCOR$^{10}$;

wherein R$^9$ is selected from the group consisting of hydrogen and C$_1$–C$_5$ alkyl; and R$^{10}$ is selected from the group consisting of C$_1$–C$_5$ alkyl and phenyl, or R$^3$ is connected to C3 with a double bond in which case R$^3$ is oxygen;

wherein R$^4$ is selected from the group consisting of hydrogen and halides; and wherein each of the bonds between C1–C2, C4–C5, C7–C8, and C16–C17 may, independently, be either single or double bonds.

24. The compound, according to claim 23, wherein R$^1$ is CH$_3$.

25. The compound, according to claim 23, wherein R$^2$ is SCH$_3$.

26. The compound, according to claim 23, wherein R$^3$ is oxygen connected to C3 with a double bond.

27. The compound, according to claim 23, wherein R$^4$ is Br.

28. The compound, according to claim 23, wherein R$^1$ is CH$_3$, R$^2$ as SCH$_3$, R$^3$ is oxygen connected to C3 with a double bond and R$^4$ is Br.

29. The compound, according to claim 23, wherein C1–C2, C4–C5 and C16–C17 are connected with double bonds.

30. The compound, according to claim 23, wherein C1–C2, C4–C5, C7–C8 and C16–C17 are connected with double bonds.

31. The compound, according to claim 23, wherein C1–C2, C4–C5 and C7–C8 are connected with double bonds.

32. The compound, according to claim 23, wherein C1–C2 and C4–C5 are connected with double bonds.

33. The compound, according to claim 23, wherein said compound has the following structure:

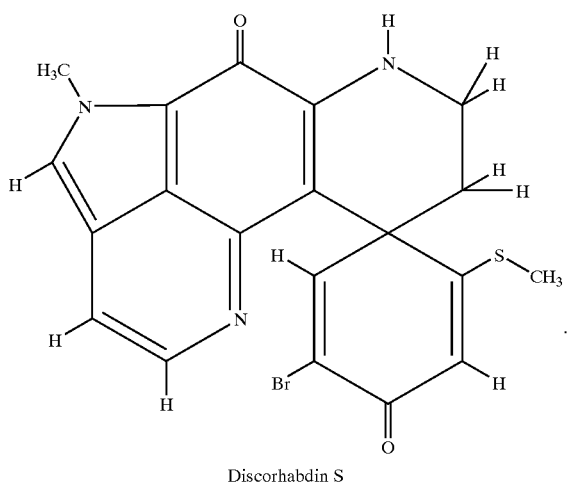

Discorhabdin S

34. The compound, according to claim 23, wherein said compound has the following structure:

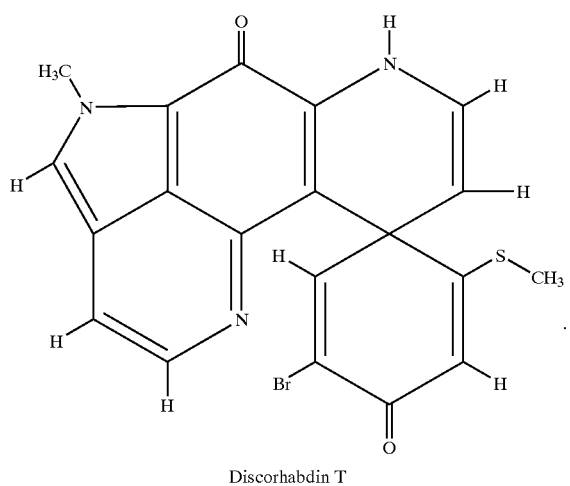

Discorhabdin T

35. The compound, according to claim 23, wherein said compound has the following structure:

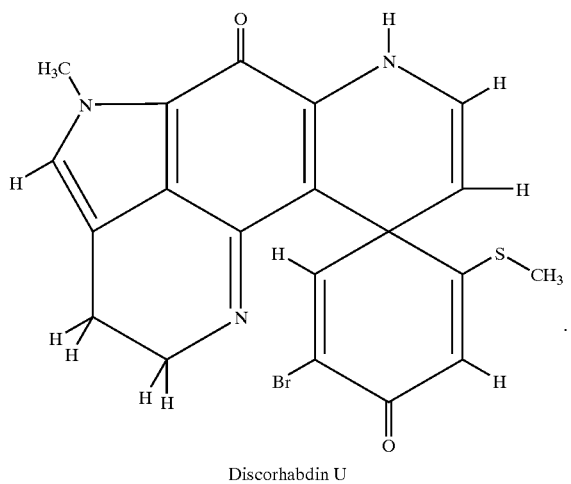

Discorhabdin U

36. The compound, according to claim 23, wherein said compound has the following structure:

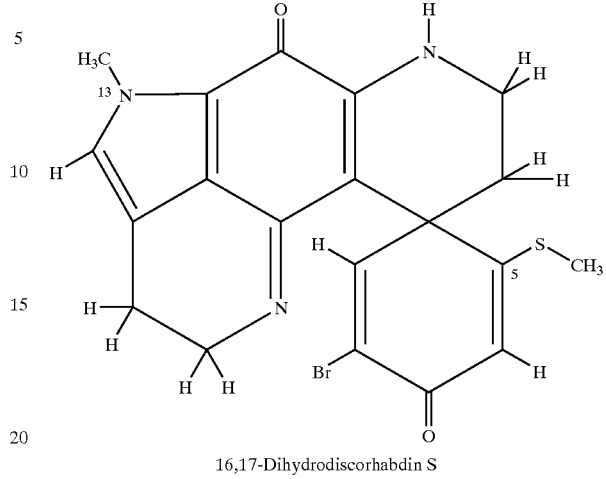

16,17-Dihydrodiscorhabdin S

37. The compound, according to claim 23, wherein said compound contains an N-methyl group at N13 and an S-methyl group at C5.

38. The compound, according to claim 23, wherein said compound contains a vinylic thiomethyl ether at the C5 position.

39. The compound, according to claim 23, wherein said salt is a Cl⁻, Br⁻, $CH_3COO^-$, $HSO_3O^-$, oxalate, citrate, or tartarate, salt.

40. The compound, according to claim 23, wherein said compound has the following spectroscopic data:

HRLSIMS ($M^+$ +H) appeared at 442.0261 ($C_{20}H_{17}^{79}BrN_3O_2S$, Δ 3.6 mmu) and 444.0470 ($C_{20}H_{17}^{81}BrN_3O_2S$)

UV (MeOH) λ max 422 (log ε 4.14), 400 (3.94), 305 (4.04), 260 (4.27), 225 (4.54) nm IR (NaCl, Neat) ν max 3385, 3043, 2924, 1858, 1637, 1602, 1543, 1498, 1348, 1318, 1240, 1017 and 735 $cm^{-1}$ $^1$H NMR (500 MHz, $CDCl_3$/10% $CD_3OD$) δ 8.08 (1H, d, J=5.8 Hz, H-17), 7.54 (1H, s, H-14), 7.50 (H, s, H-1), 7.15 (1H, d, J=5.8 Hz, H-16), 6.14 (1H, s, H-4), 4.19 (3H, s, H-22), 3.73, 3.46 (2H, m, H-8), 2.23, 2.02 (2H, m, H-7), 2.15 (3H, s, H-23)

$^{13}$C NMR (125.7 MHz, $CDCl_3$/10% $CD_3OD$) δ 176.6 (s, C-5), 175.0 (s, C-3), 165.9 (s, C-11), 155.5 (d, C-1), 146.1 (s, C-19), 145.9 (s, C-10), 142.3 (d, C-17), 130.6 (d, C-14), 123.5 (s, C-15), 122.4 (s, C-2), 119.1 (s, C-12), 118.6 (s, C-21), 117.7 (d, C-4), 111.0 (d, C-16), 104.7 (s, C-20), 47.5 (s, C-6), 37.9 (t, C-7), 37.2 (q, C-22), 36.9 (t, C-8), 14.7 (q, C-23).

41. The compound, according to claim 23, wherein said compound has the following spectroscopic data:

HREIMS ($M^+$) appeared at 438.9996 ($C_{20}H_{14}^{79}BrN_3O_2S$, Δ 1 mmu) and 440.9869 ($C_{20}H_{14}^{81}BrN_3O_2S$)

UV (MeOH) λ max 432 (log ε 3.65), 412 (3.55), 305 (3.65), 245 (3.97), 225 (4.11) nm IR (NaCl, Neat) ν max 3375, 2874, 1637, 1609, 1554, 1476, 1315, 1265, 093 and 805 $cm^{-1}$ $^1$H NMR (500 MHz, $CDCl_3$/10% $CD_3OD$) δ 8.17 (1H, d, J=5.8 Hz, H-17), 7.64 (1H, s, H-14), 7.62 (H, s, H-1), 7.30(1H, d, J=5.8 Hz, H-16), 6.43 (1H, d, J=7.5

Hz, H-8), 5.91 (1H, s, H-4), 4.25 (3H, s, H-22), 4.10 (1H, d, J=7.5Hz, H-7), 2.18 (3H, s, H-23 )

$^{13}$C NMR (125.7 MHz, CDCl$_3$/10% CD$_3$OD) δ 177.0 (s, C-5), 176.5 (s, C-3), 165.1 (s, C-11), 154.1 (d, C-1), 146.1 (s, C-19), 143.1 (d, C-17), 139.0 (s, C-10), 130.7 (d, C-14), 125.8 (d, C-8), 123.9 (s, C-15), 119.7 (s, C-12), 119.1 (s, C-21), 119.0 (s, C-2), 114.5 (d, C-4), 113.1 (d, C-16), 109.3 (s, C-20), 103.5 (d, C-7), 50.2 (s, C-6), 37.4 (q, C-22) 14.8 (q, C-23).

42. The compound, according to claim 23, wherein said compound has the following spectroscopic data:

Red powder

HRLSIMS (M$^+$ +H) appeared at 442.0275 (C$_{20}$H$_{17}$$^{79}$BrN$_3$O$_2$S, Δ 5 mmu) and 444.0052 (C$_{20}$H$_{17}$$^{81}$BrN$_3$O$_2$S)

UV (MeOH) λ max 425 (log ε 3.12), 340 (3.95), 287 (4.01), 242 (4.22), 205 (4.42) nm IR (NaCl, Neat) ν max 3328, 2924, 1637, 1602, 1558, 1479, 1435, 1280, 1010 and 668 cm$^{-1}$ $^1$H NMR (500 MHz, CDCl$_3$) δ 7.57 (1H, s, H-1), 6.99 (1H, br s, H-9), 6.63 (1H, s, H-14), 6.38 (1H, d, J=7.5 Hz, H-8), 5.88 (1H, s, H-4), 4.09 (1H, d, J=7.5 Hz, H-7), 3.93 (2H, t, J=8.0 Hz, H-17), 3.90 (3H, s, H-22), 2.58 (2H, t, J=8.0 Hz, H-16), 2.29 (3H, s, H-23)

$^{13}$C NMR (125.7 MHz, CDCl$_3$) δ 176.6 (s, C-5), 175.2 (s, C-3), 169.4 (s, C-11), 154.2 (d, C-1), 154.0 (s, C-19), 137.1 (s, C-10), 128.4 (d, C-14), 125.6 (d, C-8), 122.3 (s, C-21), 122.0 (s, C-12), 119.0 (s, C-2), 117.2 (s, C-15), 114.6 (d, C-4), 109.0 (s, C-20), 104.6 (d, C-7), 50.3 (t, C-17), 49.7 (s, C-6), 35.4 (q, C-22), 17.9 (t, C-16), 15.1 (q, C-23).

43. A pharmaceutical composition, wherein said composition comprises a compound, or a salt thereof, wherein said compound has having the following structure:

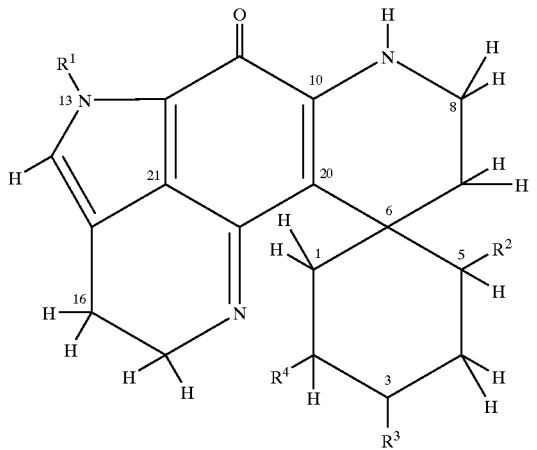

wherein R$^1$ is selected from the group consisting of hydrogen, C$_1$–C$_5$ alkyl, and COR$^5$;

wherein R$^5$ is selected from the group consisting of C$_1$–C$_5$ alkyl and phenyl;

wherein R$^2$ is selected from the group consisting of SR$^6$, SCOR$^7$, and OR$^8$;

wherein R$^6$ is selected from the group consisting of C$_1$–C$_5$ alkyl and phenyl;

R$^7$ is selected from the group consisting of C$_1$–C$_5$ alkyl and phenyl; and R$^8$ is selected from the group consisting of hydrogen, C$_1$–C$_5$ alkyl, COR$^5$ and phenyl;

wherein R$^3$ is selected from the group consisting of hydrogen, OR$^9$, and OCOR$^{10}$;

wherein R$^9$ is selected from the group consisting of hydrogen and C$_1$–C$_5$ alkyl; and R$^{10}$ is selected from the group consisting of C$_1$–C$_5$ alkyl and phenyl; or R$^3$ is connected to C3 with a double bond in which case R$^3$ is oxygen;

wherein R$^4$ is selected from the group consisting of hydrogen and halides; and wherein each of the bonds between C1–C2, C4–C5, C7–C8, and C16–C17 may, independently, be either single or double bonds.

44. The pharmaceutical composition, according to claim 43, wherein R$^1$ is CH$_3$.

45. The pharmaceutical composition, according to claim 43, wherein R$^2$ is SCH$_3$.

46. The pharmaceutical composition, according to claim 43, wherein R$^3$ is oxygen connected to C3 with a double bond.

47. The pharmaceutical composition, according to claim 43, wherein R$^4$ is Br.

48. The pharmaceutical composition, according to claim 43, wherein R$^1$ is CH$_3$, R$^2$ is SCH$_3$, R$^3$ is oxygen connected to C3 with a double bond and R$^4$ is Br.

49. The pharmaceutical composition, according to claim 43, wherein C1–C2, C4–C5 and C16–C17 are connected with double bonds.

50. The pharmaceutical composition, according to claim 43, wherein C1–C2, C4–C5, C7–C8 and C16–C17 are connected with double bonds.

51. The pharmaceutical composition, according to claim 43, wherein C1–C2, C4–C5 and C7–C8 are connected with double bonds.

52. The pharmaceutical composition, according to claim 43, wherein C1–C2 and C4–C5 are connected with double bonds.

53. The pharmaceutical composition, according to claim 43, wherein said compound has the following structure:

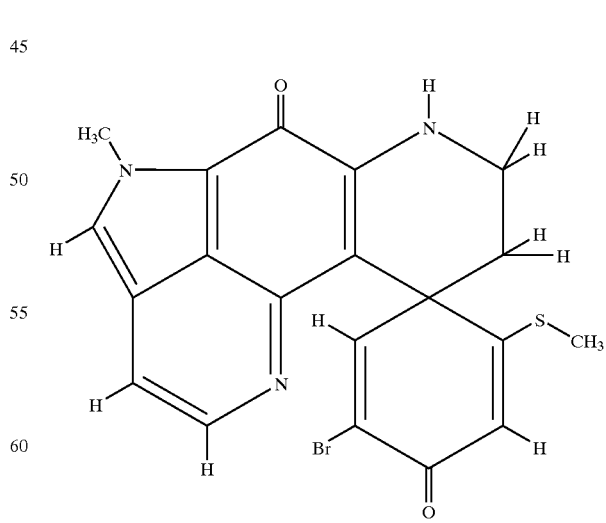

Discorhabdin S

54. The pharmaceutical composition, according to claim 43, wherein said compound has the following structure:

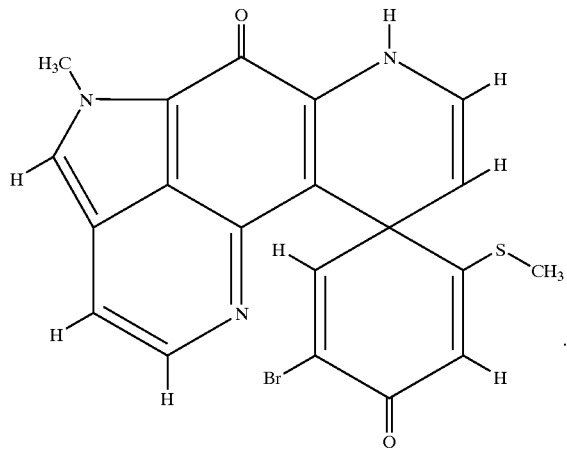

Discorhabdin T

55. The pharmaceutical composition, according to claim 43, wherein said compound has the following structure:

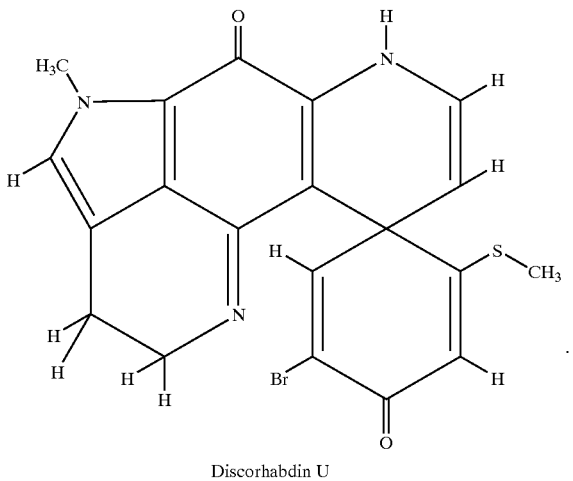

Discorhabdin U

56. The pharmaceutical composition, according to claim 43, wherein said compound has the following structure:

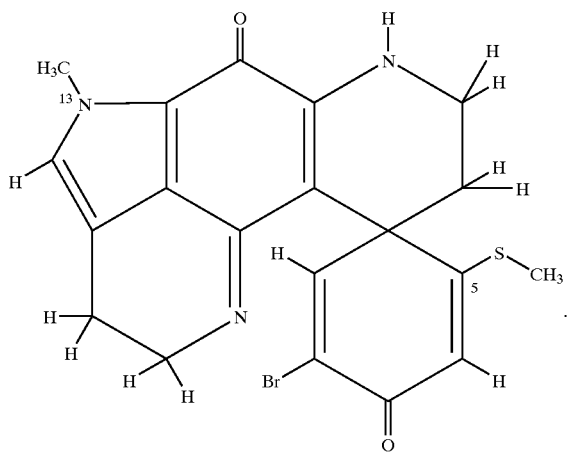

16, 17-Dihydrodiscorhabdin S

57. The pharmaceutical composition, according to claim 43, wherein said compound contains an N-methyl group at N13 and an S-methyl group at C5.

58. The pharmaceutical composition, according to claim 43, wherein said compound contains a vinylic thiomethyl ether at the C5 position.

59. The pharmaceutical composition, according to claim 43, wherein said salt is a $Cl^-$, $Br^-$, $CH_3COO^-$, $HSO_3O^-$, oxalate, citrate, or tartarate, salt.

60. The composition, according to claim 43, wherein said compound has the following spectral data:

HRLSIMS ($M^+$ +H) appeared at 442.0261 ($C_{20}H_{17}{}^{79}BrN_3O_2S$, Δ 3.6 mmu) and 444.0470 ($C_{20}H_{17}{}^{81}BrN_3O_2S$)

UV (MeOH) λ max 422 (log ε 4.14), 400 (3.94), 305 (4.04), 260 (4.27), 225 (4.54) nm IR (NaCl, Neat) ν max 3385, 3043, 2924, 1858, 1637, 1602, 1543, 1498, 1348, 1318, 1240, 1017 and 735 $cm^{-1}$ $^1$H NMR (500 MHz, $CDCl_3$/10% $CD_3OD$) δ 8.08 (1H, d, J=5.8 Hz, H-17), 7.54 (1H, s, H-14), 7.50 (H, s, H-1), 7.15 (1H, d, J=5.8 Hz, H-16), 6.14 (1H, s, H-4), 4.19 (3H, s, H-22), 3.73, 3.46 (2H, m, H-8), 2.23, 2.02 (2H, m, H-7), 2.15 (3H, s, H-23)

$^{13}$C NMR (125.7 MHz, $CDCl_3$/10% $CD_3OD$) δ 176.6 (s, C-5), 175.0 (s, C-3), 165.9 (s, C-11), 155.5 (d, C-1), 146.1 (s, C-19), 145.9 (s, C-10), 142.3 (d, C-17), 130.6 (d, C-14), 123.5 (s, C-15), 122.4 (s, C-2), 119.1 (s, C-12), 118.6 (s, C-21), 117.7 (d, C-4), 111.0 (d, C-16), 104.7 (s, C-20), 47.5 (s, C-6), 37.9 (t, C-7), 37.2 (q, C-22), 36.9 (t, C-8), 14.7 (q, C-23).

61. The composition, according to claim 43, wherein said compound has the following spectral data:

HREIMS ($M^+$) appeared at 438.9996 ($C_{20}H_{14}{}^{79}BrN_3O_2S$, Δ 1 mmu) and 440.9869 ($C_{20}H_{14}{}^{81}BrN_3O_2S$)

UV (MeOH) λ max 432 (log ε 3.65), 412 (3.55), 305 (3.65), 245 (3.97), 225 (4.11) nm IR (NaCl, Neat) ν max 3375, 2874, 1637, 1609, 1554, 1476, 1315, 1265, 093 and 805 $cm^{-1}$ $^1$H NMR (500 MHz, $CDCl_3$/10% $CD_3OD$) δ 8.17 (1H, d, J=5.8 Hz, H-17), 7.64 (1H, s, H-14), 7.62 (H, s, H-1), 7.30 (1H, d, J=5.8 Hz, H-16), 6.43 (1H, d, J=7.5 Hz, H-8), 5.91 (1H, s, H-4), 4.25 (3H, s, H-22), 4.10 (1H, d, J=7.5 Hz, H-7), 2.18 (3H, s, H-23)

$^{13}$C NMR (125.7 MHz, $CDCl_3$/10% $CD_3OD$) δ 177.0 (s, C-5), 176.5 (s, C-3), 165.1 (s, C-11), 154.1 (d, C-1), 146.1 (s, C-19), 143.1 (d, C-17), 139.0 (s, C-10), 130.7 (d, C-14), 125.8 (d, C-8), 123.9 (s, C-15), 119.7 (s, C-12), 119.1 (s, C-21), 119.0 (s, C-2), 114.5 (d, C-4), 113.1 (d, C-16), 109.3 (s, C-20), 103.5 (d, C-7), 50.2 (s, C-6), 37.4 (q, C-22), 14.8 (q, C-23).

62. The composition, according to claim 43, wherein said compound has the following spectral data:

HRLSIMS ($M^+$ +H) appeared at 442.0275 ($C_{20}H_{17}{}^{79}BrN_3O_2S$, Δ 5 mmu) and 444.0052 ($C_{20}H_{17}{}^{81}BrN_3O_2S$)

UV (MeOH) λ max 425 (log ε 3.12), 340 (3.95), 287 (4.01), 242 (4.22), 205 (4.42) nm IR (NaCl, Neat) ν max 3328, 2924, 1637, 1602, 1558, 1479, 1435, 1280, 1010 and 668 cm$^{-1}$ $^1$H NMR (500 MHz, CDCl$_3$) δ 7.57 (1H, s, H-1), 6.99 (1H, br s, H-9), 6.63 (1H, s, H-14), 6.38 (1H, d, J=7.5 Hz, H-8), 5.88 (1H, s, H-4), 4.09 (1H, d, J=7.5 Hz, H-7), 3.93 (2H, t, J=8.0 Hz, H-17), 3.90 (3H, s, H-22), 2.58 (2H, t, J=8.0 Hz, H-16), 2.29 (3H, s, H-23)

$^{13}$C NMR (125.7 MHz, CDCl$_3$) δ 176.6 (s, C-5), 175.2 (s, C-3), 169.4 (s, C-11), 154.2 (d, C-1), 154.0 (s, C-19), 137.1 (s, C-10), 128.4 (d, C-14), 125.6 (d, C-8), 122.3 (s, C-21), 122.0 (s, C-12), 119.0 (s, C-2), 117.2 (s, C-15), 114.6 (d, C-4), 109.0 (s, C-20), 104.6 (d, C-7), 50.3 (t, C-17), 49.7 (s, C-6), 35.4 (q, C-22), 17.9 (t, C-16), 15.1 (q, C-23).

* * * * *

UNITED STATES PATENT AND TRADEMARK OFFICE
CERTIFICATE OF CORRECTION

PATENT NO.    : 6,835,736 B1
DATED         : December 28, 2004
INVENTOR(S)   : Sarath Gunaskera et al.

It is certified that error appears in the above-identified patent and that said Letters Patent is hereby corrected as shown below:

Column 1,
Line 38, "Horwitz [19791]" should read -- Horwitz [1979] --.
Line 67, "Discodernolide:" should read -- Discodermolide: --.

Column 3,
Line 66, "n-butmnol" should read -- n-butanol --.

Column 5,
Line 46, "$(C_{20}H_{14}{}^{18}BrN_3O_2S)$" should read -- $(C_{20}H_{14}{}^{81}BrN_3O_2S)$ --.
Line 48, "(4.11 nm" should read -- (4.11) nm --.
Line 52, "7.62 (H, s, H-1)," should read -- 7.62 (H, s, H-1)), --.
Line 55, "2.18 (3H, s H-23)." should read -- 2.18 (3H, s, H-23). --.
Line 58, "139.0 (s, C-10) 130.7" should read -- 139.0 (s, C-10), 130.7 --.
Line 65, "HRLSLMS" should read -- HRLSIMS --.

Column 6,
Line 2, "205 (4.42 nm" should read -- 205 (4.42) nm --.
Line 11, "154 (d, C-1)," should read -- 154.2 (d, C-1), --.
Line 18, "$Cl^{31}$" should read -- (12077) nm;-- $Cl^-$ --.

Line 47, 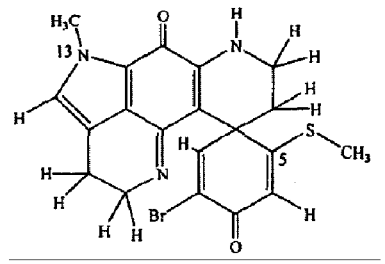 should read 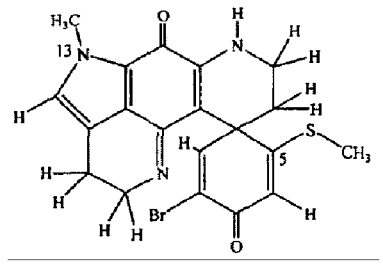

Line 58, "where $R_1$ lower" should read -- where $R_1$ = lower --
Line 66, "1,2-dihydroanalogucs" should read -- 1,2-dihydroanalogues --

Column 8,
Line 22, "bovine sernm" should read -- bovine serum --
Line 26, "106 cells/ml" should read -- $10^6$ cells/ml --
Line 34, "gentamycin su fate" should read -- gentamycin sulfate --
Line 59, "($IC_{50}$ is" should read -- ($IC_{50}$) is --
Line 62, "London, 1978." should read -- London, 1978). --

UNITED STATES PATENT AND TRADEMARK OFFICE
CERTIFICATE OF CORRECTION

PATENT NO.   : 6,835,736 B1
DATED        : December 28, 2004
INVENTOR(S)  : Sarath Gunaskera et al.

It is certified that error appears in the above-identified patent and that said Letters Patent is hereby corrected as shown below:

Column 13,
Lines 17 and 18, "7.50 (H, s, H-1)," should read -- 7.50 (H, s, H-1)), --
Lines 38 and 39, "7.62 (H, s, H-1)," should read -- 7.62 (H, s, H-1)), --

Column 16,
Lines 45 and 46, "7.50 (H, s, H-1)," should read -- 7.50 (H, s, H-1)), --
Lines 66 and 67, "7.62 (H, s, H-1)," should read -- 7.62 (H, s, H-1)), --

Column 20,
Line 23, "7.50 (H, s, H-1)," should read -- 7.50 (H, s, H-1)), --
Line 47, "7.62 (H, s, H-1)," should read -- 7.62 (H, s, H-1)), --

Signed and Sealed this

Twelfth Day of July, 2005

JON W. DUDAS
*Director of the United States Patent and Trademark Office*